US00PP07809P

United States Patent [19]

Fleming

[11] Patent Number: Plant 7,809

[45] Date of Patent: Feb. 25, 1992

[54] KALANCHOE PLANT NAMED PIONEER

[75] Inventor: Margaret M. Fleming, Soquel, Calif.

[73] Assignee: The Plant Company, Soquel, Calif.

[21] Appl. No.: 607,375

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A Kalanchoe plant named Pioneer particularly characterized by its multi-colored inflorescences, with individual florets opening to yellows, golds, oranges, and shade between, and maintaining such colors through maturity; flower diameter of up to 15 mm at maturity; flowering response of from 10 weeks in summer to 12 weeks in winter after start of short days; floriferous, with excellent display of many flowers; excellent keeping quality of both flowers and foliage; excellent free branching with or without pinching; intermediate vigor with short internodes; fine textured, medium sized, nicely serrated foliage; good response to B-9 to reduce peduncle elongation, and adaptability to various pot sizes.

2 Drawing Sheets

The present invention relates to a new and distinctive cultivar of Kalanchoe plant, botanically known as *Kalanchoe blossfeldiana* Poelln., and referred to by the cultivar name Pioneer.

Pioneer, identified as 577-450, is a product of a planned breeding progam which had the objective of creating new Kalanchoe cultivars for year-round commercial production having an earlier flowering response, good branching yet compact flowering plants, suitable for flowering in pots ranging from 10 to 15 cm, and having good flower and foliage keeping quality.

Pioneer was originated by the inventor Margaret M. Fleming from a controlled selfing of the parent plant, an unnamed seedling identified as 402-041, produced from the crossing of Cinnabar and Fortyniner, in Half Moon Bay, Calif., in 1984.

Pioneer was discovered and selected as one flowering plant within the progeny of the stated selfing by Margaret M. Fleming in February of 1986 in a controlled environment in Soquel, Calif.

The first act of asexual reproduction of Pioneer was accomplished when vegetative cuttings were taken from the initial selection in July 1986 in a controlled environment in Soquel, Calif., by Margaret M. Fleming.

Horticultural examination of controlled flowerings of successive plantings has shown that the unique combination of characteristics as herein disclosed for Pioneer are firmly fixed and are retained through successive generations of asexual reproduction. Pioneer has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Pioneer which, in combination, distinguish this Kalanchoe as a new and distinct cultvar:

1. Multi-colored inflorescences, with individual florets displaying colors ranging from bright yellows to golds to oranges, and shades of those colors. These colors are maintained through maturity and do not fade.

2. Flower diameter of 13 to 15 mm at maturity.
3. Flowering response of from 10 weeks in summer to weeks in winter after start of short days.
4. Floriferous, with excellent display of many flowers.
5. Excellent keeping quality of both flowers and foliage, with each floret lasting more than two weeks under normal conditions of finishing and holding.
6. Branches freely with or without pinching.
7. Vigorous with fine textured, medium sized, nicely serrated foliage.
8. Responsive to B-9 to reduce peduncle elongation.
9. Proper scheduling makes this new cultivar suitable for production in 10 cm to 15 cm pots.

The accompanying colored photographic drawings show typical inflorescence and leaf characteristics of Pioneer, with colors being as nearly true as possible with illustrations of this type.

Sheet 1 is a color photograph of Pioneer grown as a non-pinched flowering Kalanchoe in a 10 cm pot.

Sheet 2 is a black and white photograph showing the leaves of Pioneer at three stages of development (mature, intermediate and immature).

The combination of multi-colored inflorescence, foliage size and shape and keeping quality of flowers and foliage is not represented in any commercial cultivar known to the inventor. The most similar to Pioneer is the cultivar Goldstrike, disclosed in U.S. Plant Pat. No. 6,632. Similar traits are plant habit, vigor, responsiveness to B-9 and adaptability to various pot sizes. In comparison to Goldstrike, Pioneer has an earlier flowering response by at least one week, far superior keeping quality than Goldstrike, and the noted multi-colored inflorescence and is also much taller. Although a few of the petals of Goldstrike fade from their bright yellow-orange color to a more orange tone, the color at opening is uniform. As noted, Pioneer exhibits its multi-color characteristics from opening through maturity.

In comparison to the paternal grandparent Fortyniner, the flower color of Fortyniner is yellow, fading to tan, as contrasted with the multi-colored flowers of Pioneer, with individual florets being yellow, gold, orange and shades of rose. This color variation presents a very striking display. In addition, the flowering response of Pioneer is a week earlier under the same growing conditions, and the flowers and foliage of Pioneer are very long lasting, as clearly contrasted to the flowers and foliage of Fortyniner which are well known to degrade rapidly. Both Pioneer and Fortyniner are intermediate in vigor, equally responsive to growth regulation, branch well with or without a pinch, and are adaptable to various pot sizes.

Pioneer can also be compared with the maternal grandparent Cinnabar. Again, its multi-colored flowers in the colors indicated are contrasted to the uniform orange/red flower color of Cinnabar. The flowers and foliage of Pioneer are exceptionally long lasting, as compared with the flowers of Cinnabar which fade fast, and its foliage which is only average in keeping quality. Although the foliage color of both clutivars are about the same, the foliage form of Pioneer is more lanceolate, more serrated, and has better substance. A still further distinction is in the flowering response period to short day treatment, with Pioneer being a full week later than Cinnabar. Both Pioneer and Cinnabar are average in height, intermediate in growth and vigor, equally responsive to growth regulation, branch well with or without a pinch, and are adaptable to various pot sizes.

In the following description color references are made to The Royal Horticultural Society Colour Chart. The color values were determined on plant material grown as a non-pinched pot plant in a 10 cm pot in Soquel, Calif., on Oct. 2, 1988.

Classification:

*Botanical.*—*Kalanchoe blossfeldiana* Poelln. cv. Pioneer.

*Commercial.*—Flowering pot Kalanchoe.

Parentage: Controlled selfing of an unnamed seedling, 402-041.

Propagation:

(A) *Type cutting.*—Short tip cutting, with stems up to 2 cm.

(B) *Time to root.*—10 days at 21° C. in summer; 14 days at 21° C. in winter.

(C) *Rooting habit.*—Many very fine roots, fibrous.

Plant Description:

(A) *Form.*—Medium tall upright growth. Growing and scheduling practices can produce a small plant in a 10 cm pot up to a larger plant in a 15 cm pot.

(B) *Habit of growth.*—Rate of growth moderate for this type of plant. Generally, shoots are formed at every node, with intermodes being 15–30 mm for a vegetative natural plant; height of plant above 10 cm pot, approximately 20–30 cm, based on 3–4 applications of 3500 ppm B-9 SP growth regulator.

(C) *Foliage description.*—Leaves simple, opposite, slightly lobed. 1. Size: Average full grown leaf in a 10 cm flowering pot is 110 mm long×65 mm wide. 2. Shape: Ovate to elliptic, apex obtuse to slightly pointed, base attenuate.

3. Texture: Glabrous, coriaceous, succulent. 4. Margin: Sinuate to crenate. 5. Color (mature foliage): Upper surface 147A; under surface 147B. 6. Durability: Excellent; no degradation observed even on the lower foliage of plants retained for months beyond their normal life expectancy. The foliage of Pioneer foliage is a great improvement over the foliage of the older yellow varieties Fortyniner, Fujii, and Goldstrike. 7. Foliar diseases: Resistant or immune to Powdery Mildew. Chlorosis has not been observed even though Fortyniner is a parent. Necrotic spots, tip die-back, stem rot and root rot have not been observed.

Flowering Description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (10–15 mm) will continue for two months or more. Individual flowers last two weeks or more after opening. No perceived fragrance.

(B) *Flowering response.*—Flowering time under controlled daylength after start of short days is 10 weeks in summer to 12 weeks in winter.

(C) *Flowers borne.*—Compound dichasial cymes; peduncle 5–15 cm, diameter 408 mm; pedicel length 5–7 mm, diameter greater than 1 mm.

(D) *Quantity of flowers.*—Very floriferous; floret count 80–100 per primary inflorescence, 400–500 total per 10 cm pot plant, commercial culture.

(E) *Petals.*—1. Shape: Slightly pointed to almost round. 2. Color: Upper surface: Petals open at all of colors 10B, 16C-16D, 23C-23D, and 24C-24D. There is little fading during maturity. Under surface: Opening at 10B, 16D to 23D. 3. Number of petals: 4, united in corolla. 4. Flower diameter: 13 to 15 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigam shape: Flat, crystalline, color greenish white. b. Style color: Light green. c. Ovaries: 4-celled, color light green.

(G) *Flower diseases.*—None noted to date; resistant to Botrytis; no problems with color breaking or excess fading.

I claim:

1. A new and distinct Kalanchoe plant named Pioneer, as described and illustrated.

* * * * *

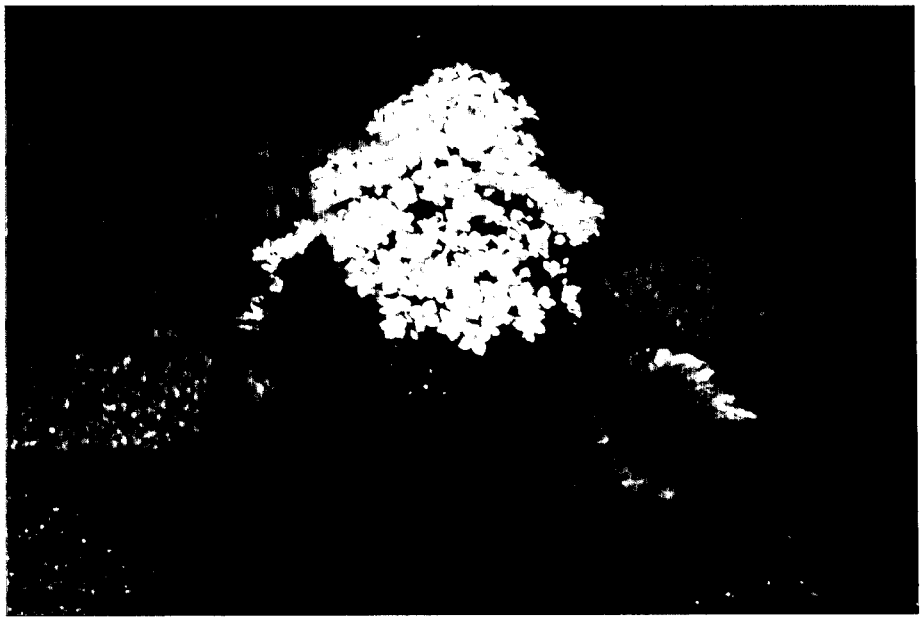

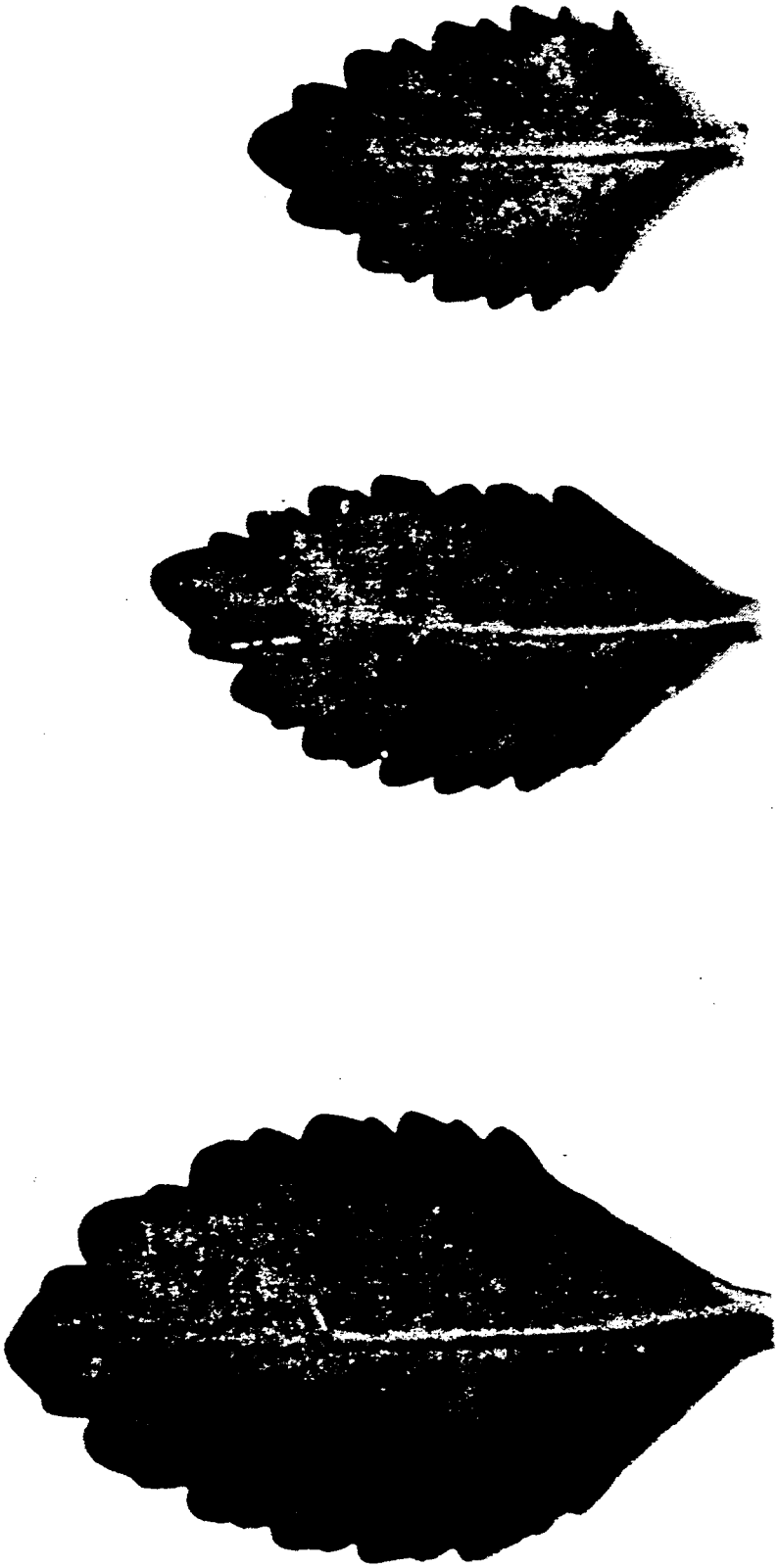
PIONEER